United States Patent [19]

Liu

[11] Patent Number: 5,667,609
[45] Date of Patent: Sep. 16, 1997

[54] METHOD FOR ATTACHING BARRIER CUFFS TO DISPOSABLE ABSORBENT ARTICLE

[75] Inventor: Vincent B. Liu, Cincinnati, Ohio

[73] Assignee: The Procter & Gamble Company, Cincinnati, Ohio

[21] Appl. No.: 601,483

[22] Filed: Feb. 14, 1996

[51] Int. Cl.[6] .................................................. A61F 13/15
[52] U.S. Cl. ..................... 156/73.1; 156/73.5; 156/290; 156/291; 156/308.4
[58] Field of Search ............................. 156/73.1, 73.5, 156/163, 164, 229, 290, 291, 308.2, 308.4

[56] References Cited

U.S. PATENT DOCUMENTS

| | | | |
|---|---|---|---|
| 4,081,301 | 3/1978 | Buell | 156/164 |
| 4,525,229 | 6/1985 | Suzuki et al. | 156/161 |
| 4,626,305 | 12/1986 | Suzuki et al. | 156/164 |
| 4,695,278 | 9/1987 | Lawson | 604/385 |
| 4,915,767 | 4/1990 | Rajala et al. | 156/440 |
| 5,030,303 | 7/1991 | Cucuzza | 156/164 |
| 5,032,120 | 7/1991 | Freeland et al. | 604/385.2 |
| 5,213,645 | 5/1993 | Nomura et al. | 156/164 |
| 5,413,654 | 5/1995 | Igaue et al. | 156/161 |
| 5,496,428 | 3/1996 | Sageser et al. | 156/73.1 |
| 5,577,540 | 11/1996 | Sageser | 156/226 |

*Primary Examiner*—James Sells
*Attorney, Agent, or Firm*—Kevin C. Johnson; Steven W. Miller; Jacobus C. Rasser

[57] ABSTRACT

A method for attaching a barrier cuff to an absorbent article. The first step is to provide an absorbent article having a longitudinal centerline and a transverse centerline perpendicular to the longitudinal centerline. A barrier leg cuff having a first edge and a second edge is provided. At least one of the edges of the barrier cuff is maintained parallel to the longitudinal centerline of the absorbent article. The barrier cuff is then bonded to the absorbent article along a juncture line that extends in a curved configuration with respect to the longitudinal centerline of the absorbent article.

17 Claims, 7 Drawing Sheets

METHOD FOR ATTACHING BARRIER CUFFS TO DISPOSABLE ABSORBENT ARTICLE

FIELD OF THE INVENTION

The present invention relates to disposable absorbent articles, such as disposable diapers, having barrier cuffs, and more particularly to a method for attaching the barrier cuffs to the disposable absorbent article.

BACKGROUND OF THE INVENTION

Disposable absorbent articles, such as diapers, frequently utilize one or both of two types of leg cuffs, gasket leg cuffs and barrier leg cuffs. Gasket leg cuffs are used to seal the leg openings of the article about the wearer and to help prevent the leakage of body exudates from the article at the leg openings. For example, U.S. Pat. No. 3,860,003 issued to Buell on Jan. 14, 1975, teaches a diaper having an elastically contractible side portion. U.S. Pat. No. 4,333,782 issued to Pieniak on Jun. 8, 1982 and U.S. Pat. No. 4,450,026 issued to Pieniak et al. on May 22, 1984 teach diapers having an elastic film ribbon incorporated into the marginal edges of the diapers.

Barrier leg cuffs are utilized to provide improved containment of body exudates within the disposable absorbent article. For example, U.S. Pat. No. 4,704,115 issued to Buell on Nov. 3, 1987 teaches a disposable garment having side edge leakage guard gutters which obviate inversion and then folding during use by not encircling the thighs of the wearer. U.S. Pat. No. 4,808,178 issued to Aziz et al. on Feb. 28, 1989 teaches a disposable article having leakage resistant flaps which are nonabsorbent and liquid-impermeable.

Other variations of barrier cuffs have been proposed, such as U.S. Pat. No. 4,795,452 issued to Blaney et al. on Jan. 3, 1989. This reference teaches a disposable article having a cuff member with a cantilevered flap which provides a liquid-impermeable seal, a barrier wall which retards the flow of exudates and gasketing action about the legs of the wearer. U.S. Pat. No. 4,795,454 issued to Dragoo on Jan. 3, 1989 teaches a disposable absorbent article having a barrier cuff with a distal edge and a proximal edge, with spacing means disposed at the distal edge and a seal formed at the proximal edge.

In order to improve the performance of barrier leg cuffs, complex methods and equipment have been used in order to apply elastic members in a curved manner to the disposable absorbent article in order to better fit around the legs of the wearer. However, the methods and the equipment used to apply the elastic members in a curved manner are both complex and costly. Therefore, it is an object of the present invention to provide an improved method for attaching barrier leg cuffs to absorbent articles in a curved manner.

SUMMARY OF THE INVENTION

The present invention provides a method for attaching a barrier cuff to an absorbent article in a curved manner. The first step is to provide an absorbent article comprising a topsheet, a backsheet secured to the topsheet, and an absorbent core positioned between the topsheet and the backsheet. The absorbent article has a longitudinal centerline and a transverse centerline perpendicular to said longitudinal centerline. A barrier leg cuff is then provided which comprises a first edge and a second edge. At least one of the edges of the barrier cuff is maintained parallel to the longitudinal centerline of the absorbent article. The barrier cuff is then bonded to the absorbent article along a juncture line that extends in a curved configuration with respect to the longitudinal centerline of the absorbent article.

BRIEF DESCRIPTION OF THE DRAWINGS

While the specification concludes with claims particularly pointing out and distinctly claiming the subject matter which is regarded as forming the present invention, it is believed that the present invention will be better understood from the following description in conjunction with the accompanying drawings, in which like reference numerals identify like elements and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article, (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, and the like.

Figure 1:
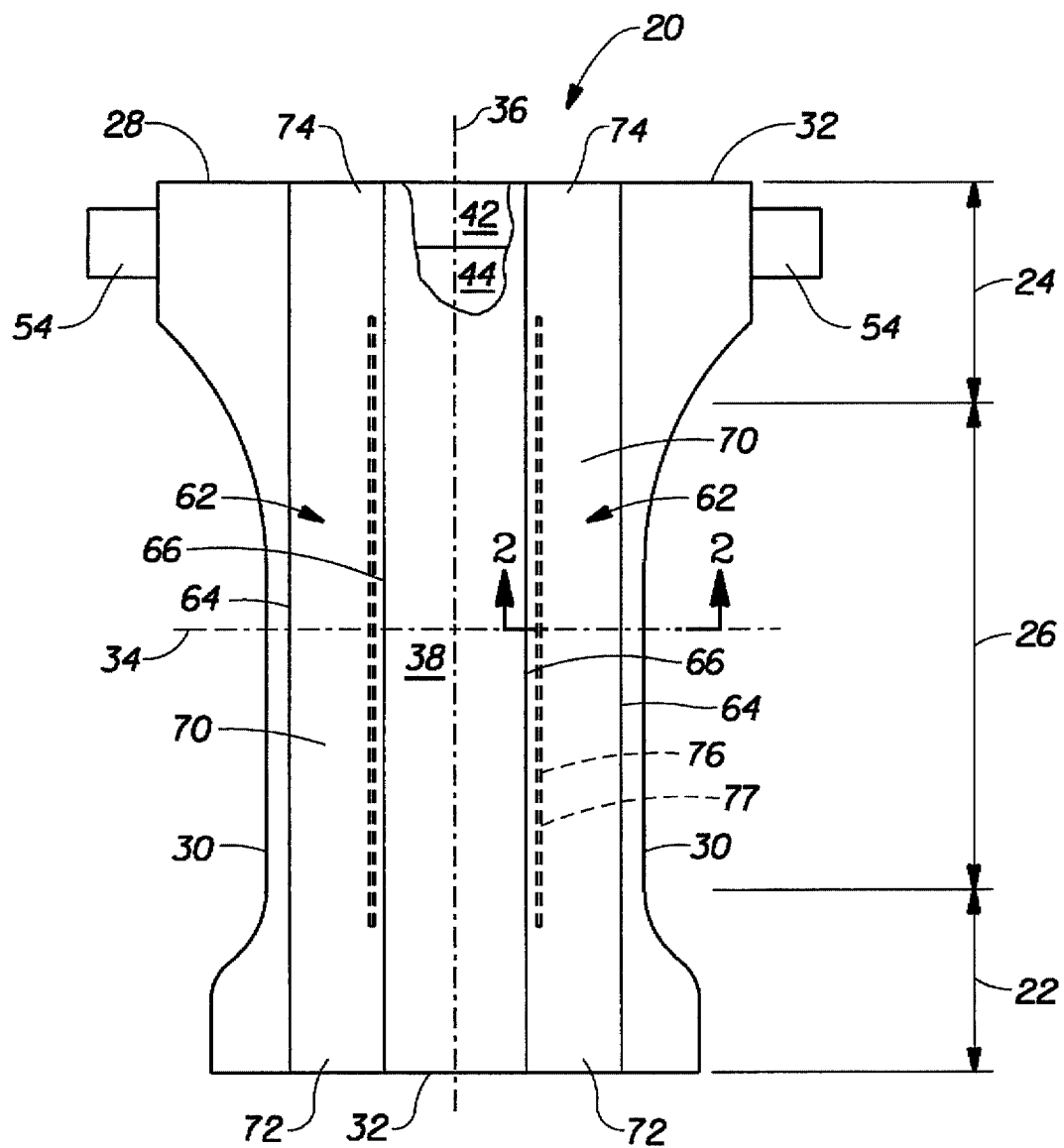
FIG. 1 is a plan view of a disposable diaper embodiment of the present invention having portions cut-away to reveal the underlying structure.

FIG. 1 is a plan view of the diaper 20 of the present invention in its flat-out, uncontracted state (i.e., with all elastic induced contraction pulled out) with portions so of the structure being cut away to more clearly show the construction of the diaper 20 and with the portion of the diaper 20 which contacts the wearer facing the viewer. The diaper 20 is shown in FIG. 1 to have a front waist region 22, a back waist region 24, a crotch region 26 positioned between the front waist region 22 and the back waist region 24, and a periphery 28 which is defined by the outer edges of the diaper in which the longitudinal edges are designated 30 and the end edges are designated 32. The diaper 20 additionally has a lateral or transverse centerline which is designated 34 and a longitudinal centerline designated 36 which is perpendicular to the lateral centerline 34.

The diaper 20 comprises a liquid pervious topsheet 38, a liquid impervious backsheet 42 joined with the topsheet 38, an absorbent core 44 positioned between the topsheet 38 and the backsheet 42, a pair of tape tab fasteners 54, barrier cuffs 62 each having a first edge 64, a second edge 66, an inboard surface 68 (shown in FIG. 2), an outboard surface 70, a first end 72 and a second end 74; and spacing means 76 such as spacing elastic member 77 for spacing the second edge 66 away from the topsheet 38. The diaper 20 additionally comprises a juncture line 78 (shown in FIG. 2), such as a glue bead 79 for bonding the barrier cuffs 62 to the disposable diaper 20. The glue bead 79 is preferably a hot melt adhesive such as marketed by Findley Adhesives, Inc. Other suitable means for bonding the barrier cuffs 62 to the disposable diaper 20 along juncture line 78 include but are not limited to ultrasonic bonding, heat bonding, pressure bonding, friction bonding and autogenous bonding.

FIG. 1 shows a preferred embodiment of the diaper 20 in which the topsheet 38 and the backsheet 42 are coextensive and have length and width dimensions generally larger than those of the absorbent core 44. The topsheet 38 is associated with and superposed on the backsheet 42 to thereby form the periphery 28 of the diaper 20. The periphery 28 defines the outer perimeter or, in other words, the edges of the diaper 20. The periphery 28 comprises the end edges 32 and the longitudinal edges 30.

Figure 2:
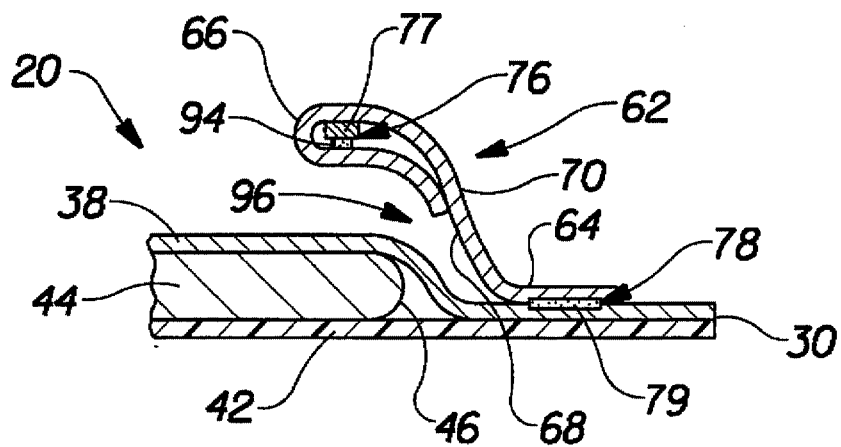
FIG. 2 is a fragmentary sectional view taken along section line 2—2 of FIG. 1.

FIG. 2 is fragmentary section to be taken along line 2—2 of FIG. 1 and depicts the diaper construction in the crotch region 26 of the diaper 20 as it is shaped before being applied to the wearer (i.e., the diaper 20 is subjected to elastic contraction. The absorbent core 44 is disposed between the topsheet 38 and the backsheet 42; both the topsheet 38 and the backsheet 42 extend beyond the side edge 46 of the absorbent core 44. The barrier cuff 62 is shown as being formed by bonding an element to the topsheet 38 between the longitudinal edge 30 of the diaper 20 and the side edge 46 of the absorbent core 44. The first edge 64 of the barrier cuff 62 is bonded to the topsheet 38 along juncture line 78. The spacing elastic members 77 are enclosed in a tunnel that is formed when an end of the barrier cuff element is folded back upon itself. The spacing elastic member 77 is secured in the barrier cuff 62 by elastic attachment means 94. The second edge 66 of the barrier cuff is spaced away from the topsheet 38 by the elastic gathering action of the spacing elastic members 77. A channel 96 is thereby formed by at least the first edge 64, the second edge 66 and the inboard surface 68 of the barrier cuff 62. The channel 96 is shown as being ready to restrain, contain and hold body exudates until the diaper 20 is removed from the wearer.

Each barrier cuff 62 is a flexible member having a first edge 64, and second edge 66, an inboard surface 68 and an outboard surface 70. As used herein, the term "flexible" refers to materials which are compliant and will readily conform to the general shape and contours of the body. In addition, if the spacing means 76 comprise spacing elastic members 77, the barrier cuffs 62 must be contractible so that the second edge 66 may be sufficiently spaced away from the topsheet 38 so that a channel 96 is formed to restrain, contain and hold body exudates within the article. The barrier cuffs 62 may be manufactured from a wide variety of materials such as polypropylene, polyester, rayon, nylon, foams, plastic films, formed films, and elastic foams. A number of manufacturing techniques may be used to manufacture the barrier cuff 62. For example, the barrier cuff 62 may be a woven, nonwoven, spunbonded, carded, or the like.

A preferred embodiment of the diaper 20 shown in FIG. 1 is provided with the barrier cuff 62 joined to the topsheet 38. The term "joined" includes any means for affixing the barrier cuff 62 to the diaper 20, and includes embodiments where the barrier cuff 62 is a separate element which is directly or indirectly attached to the diaper 20. The barrier cuff 62 may be joined to the backsheet 42, the absorbent core 44, the topsheet 38 or any combinations of these or other elements of the diaper 20. In a preferred embodiment, the barrier cuff 62 is integral with the topsheet 38. The integral barrier cuff 62 is preferably formed by a single strip of material which is bonded to the topsheet along juncture line 78 by glue bead 79, the second edge 66 being formed by folding an end of the material back upon itself.

The second edge 66 is preferably disposed inboard of the first edge 64 to present a more effective barrier against the flow of exudates. The second edge 66 is preferably not secured to any other element in at least the crotch region 26 of the diaper 20 so that it may be spaced away from the topsheet 38. The second edge 66 is preferably spaced away from the topsheet 38 so that the barrier cuff 62 may form a channel 96 to enhance the containment characteristics of the diaper 20.

The barrier cuff 62 may be rendered liquid impermeable so as to prevent the strike through of body exudates. A liquid impermeable barrier cuff 62 retards the movement of liquids through the barrier cuffs 62, thereby making it more leakage resistant. The barrier cuff 62 may be rendered liquid impermeable in any manner well known in the art such as selectively treating the barrier cuff, untreating the barrier cuff, or by securing a separate material to the barrier cuff 62. Further, the barrier cuff 62 may permit vapors to escape (i.e., breathable) while still preventing exudates from passing through the barrier cuff 62.

The spacing means 76 for spacing the second edge 66 away from the topsheet 38 is any member which gathers, contracts, stiffens, shortens, or otherwise acts on the barrier cuff 62 so as to cause a channel 96 to be formed along the barrier cuff 62 to provide a constraint against the leakage of exudates.

As shown in FIG. 1, the spacing means 76 preferably comprises spacing elastic member 77 secured adjacent the second edge 66 inside the barrier cuff 62. The spacing elastic member 77 is preferably secured to the barrier cuff 62 in an elastically contractible condition so that in a normally unstrained configuration, the spacing elastic member 77 effectively contracts or gathers the barrier cuff 62. The spacing elastic member 77 can be secured to the barrier cuff 62 in an elastically contractible condition in at least two ways as is discussed in U.S. Pat. No. 3,860,003 issued to Buell on Jan. 14, 1975. In addition, the length of the spacing elastic member 77 in general is dictated by the diaper design. In the embodiment illustrated in FIG. 1, the spacing elastic member 77 extends essentially the entire length of the barrier cuff 62 in the crotch region 26, although other lengths are cognizable.

As shown in FIG. 2, the spacing elastic member 77 is associated with the barrier cuff 62 by securing it within the barrier cuff with elastic attachment means 94. While the spacing elastic members 77 may be secured to the barrier cuff 62 adjacent only the ends of the elastic spacing member 77, it is preferable to secure the entire length of the spacing elastic member 77 to the barrier cuff 62. The elastic attachment means 94 herein are preferably glue beads made of hot melt adhesive such as marketed by Findley Adhesives Inc. A more detailed description of the manner in which the spacing elastic members 77 may be positioned and secured to the barrier cuff 62 can be found in U.S. Pat. No. 4,081,301 issued to Buell on Mar. 28, 1978, and in U.S. Pat. No. 4,253,461 issued to Strickland and Visscher on Mar. 3, 1981, both of which are incorporated herein by reference. It should also be noted that one or more spacing elastic members 77 can be used to elasticize each barrier cuff 62. In addition, the spacing elastic members 77 may take a multitude of configurations. For example, the width of the spacing elastic member 77 may be varied; the spacing elastic members may comprise a single strand or several strands of elastic material; or the spacing elastic member 77 may be rectilinear or curvilinear. Still further, the spacing elastic member 77 may be affixed to the barrier cuffs 62 in any of several ways which are well known in the art. For example, the spacing elastic members may be ultrasonically bonded or heat sealed into the barrier cuff 62 using a variety of bonding patterns, or the spacing elastic members 77 may simply be glued to the barrier cuffs 62.

Figure 2A:
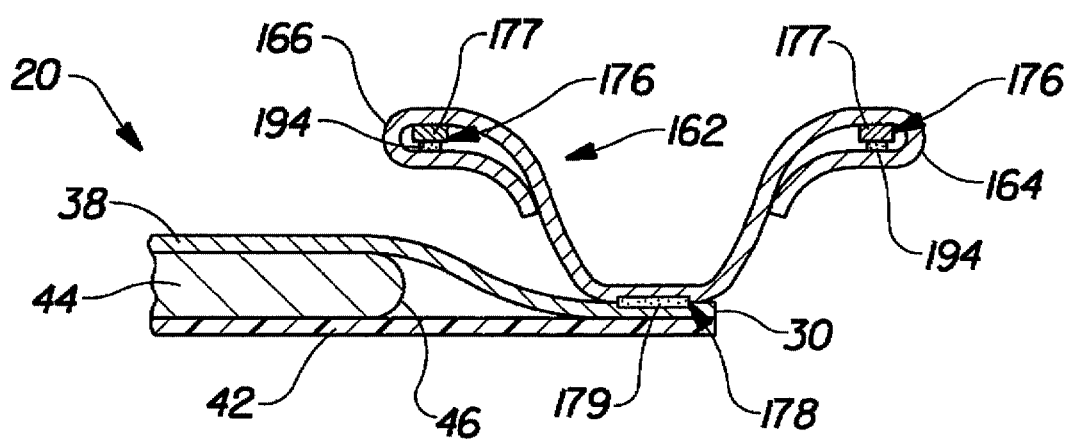
FIG. 2A is a fragmentary sectional view of a diaper showing an alternative embodiment of a barrier cuff of the present invention.

FIG. 2A is a fragmentary section of a diaper 20 showing an alternative embodiment of a barrier cuff 162 of the present invention. The diaper 20 comprises a topsheet 38, a backsheet 42 joined to the topsheet 38, and an absorbent core 44 positioned between the topsheet 38 and the backsheet 42. The barrier cuff 162 is shown as being formed by bonding an element to the topsheet 38 between the longitudinal edge 30 of the diaper 20 and the side edge 46 of the absorbent core 44. The barrier duff 162 comprises a first edge 164, a second edge 166 and spacing means 176 such as such as spacing elastic members 177. Barrier cuff 162 is bonded to the diaper 20 along juncture line 178 by means of a glue bead 179, preferably of hot melt adhesive.

The spacing elastic members 177 are each enclosed in a tunnel that is formed when an end of the barrier cuff element is folded back upon itself. The spacing elastic members 177 are secured to the barrier cuff 162 by elastic attachment means 194. The second edge 166 of the barrier cuff 162 is spaced away from the topsheet 38 by the elastic gathering action of the spacing elastic members 177.

The second edge 166 is preferably disposed inboard of the longitudinal edge 30 of the diaper 20. The first edge 164 is shown disposed outboard of the longitudinal edge of the diaper 20.

Figure 3:
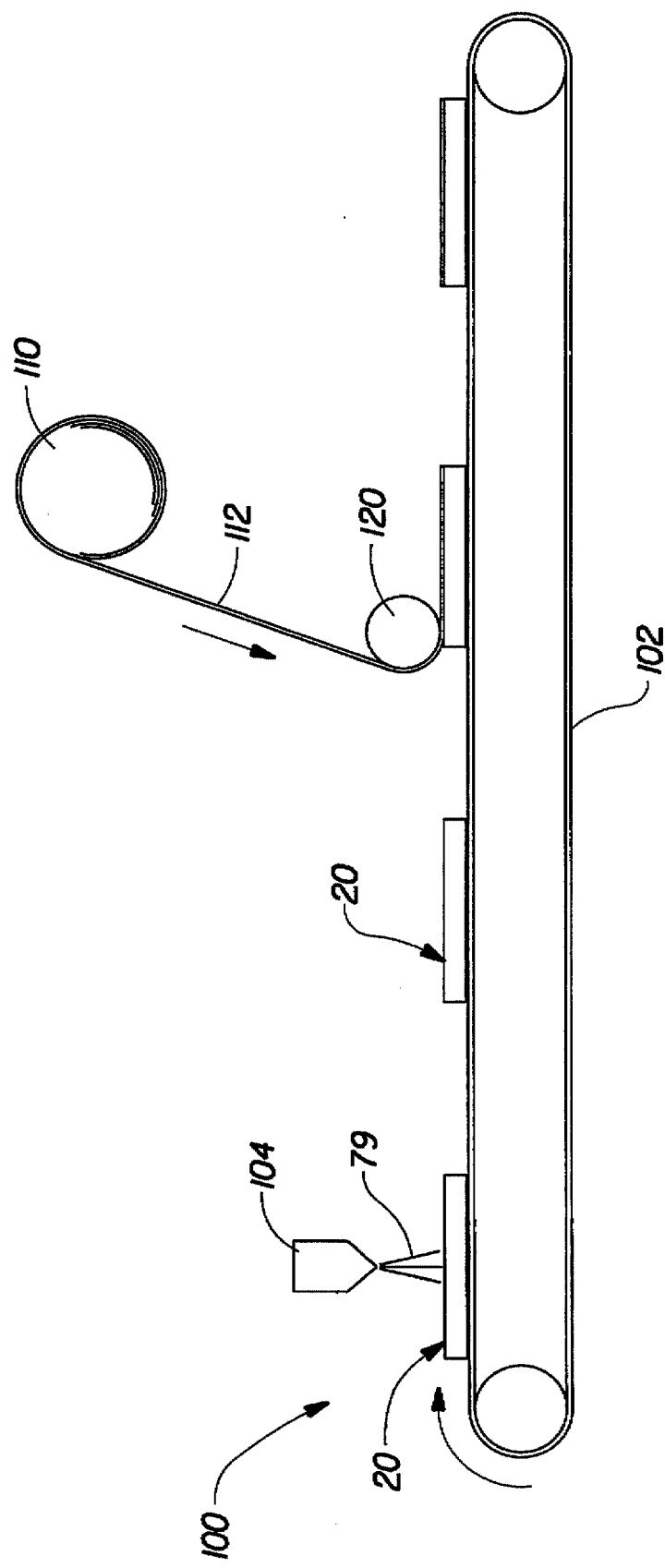
FIG. 3 is a simplified sectional side elevational view showing the method for attaching the barrier cuff to the disposable diaper of the present invention.

The barrier leg cuffs may be secured to the disposable diaper 20 utilizing apparatus 100 shown in FIG. 3. Examining apparatus 100 in greater detail, a plurality of disposable diapers 20 are provided which preferably comprise a topsheet, a backsheet joined to the topsheet, and an absorbent core positioned between the topsheet and the backsheet. The disposable diapers 20 are fed on conveyor 102 toward adhesive applicator 104. In the embodiment shown in FIG. 3 adhesive applicator 104 applies adhesive 79 onto the topsheet of disposable diaper 20 in a curved configuration. The adhesive applicator 104 may be any suitable means known in the art for applying adhesive to a substrate in a curved configuration. Examples of suitable applicators include sprayers, slot coaters, and printers. The adhesive 79 is applied by adhesive applicator 104 to the disposable diaper 20 in a curved configuration with respect to the longitudinal centerline of the disposable diaper so as to form a curved juncture line.

Figure 4:
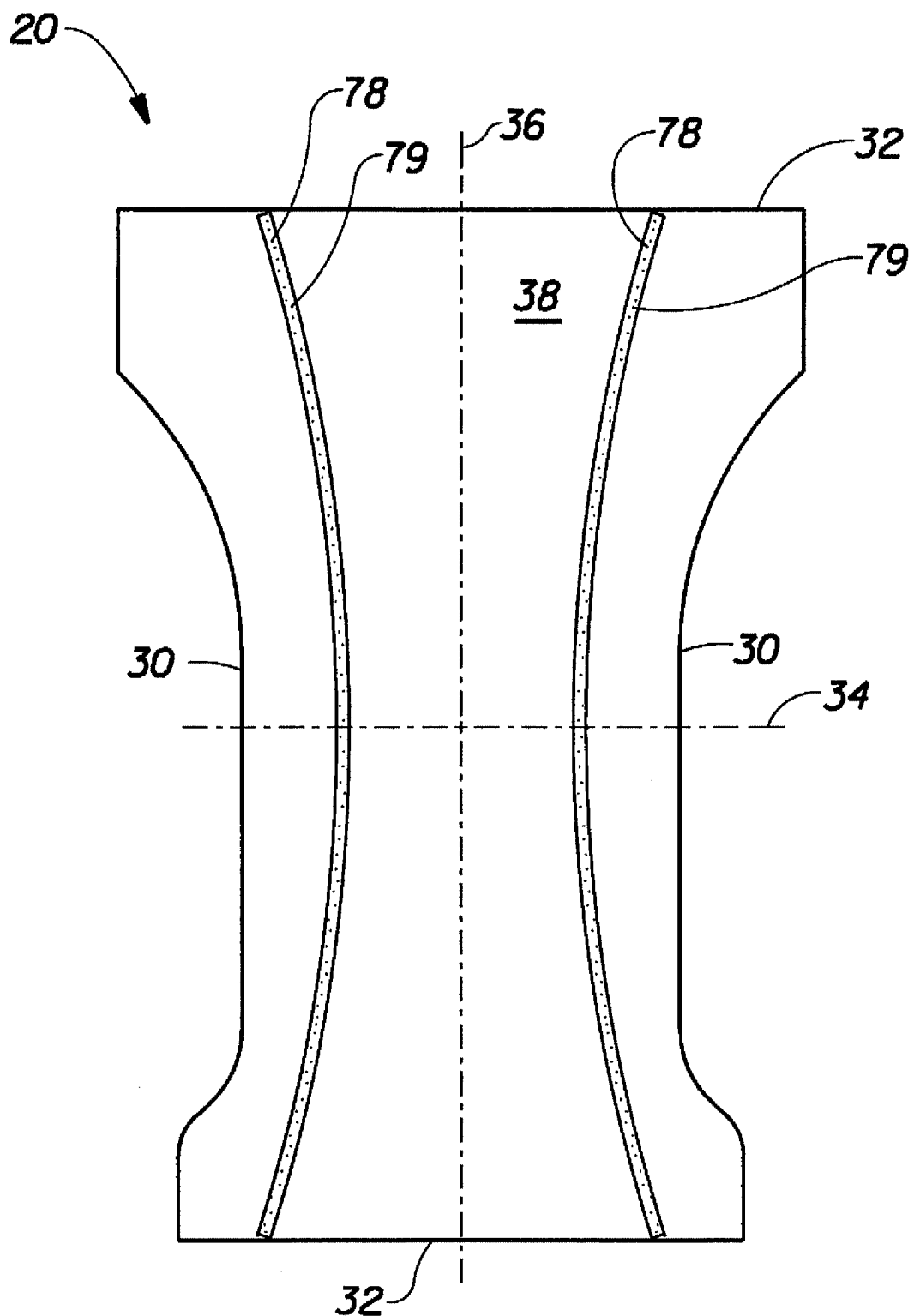
FIG. 4 is a plan view of a disposable diaper showing the disposable diaper after the adhesive has been applied to the diaper in a curved configuration.

FIG. 4 is a plan view of the disposable diaper 20 after the adhesive 79 has as been applied to diaper 20 by adhesive applicator 104. As can be seen in FIG. 4, glue beads of hot melt adhesive 79 have been applied to the topsheet 38 of the diaper 20 in a curved configuration with respect to the longitudinal centerline 36 of the diaper 20 so as to form a curved juncture line 78. In the embodiment shown in FIG. 4, the curved juncture lines 78 are closest to one another near the transverse centerline 34 and are spaced farthest from one another at the respective end edges 32 of the diaper 20. While only a preferred configuration for curved juncture line 78 is shown, other curved configurations may also be suitable so long as the juncture line 78 has a configuration other than parallel to the longitudinal centerline 36 of the diaper 20.

In the embodiment shown in FIG. 4, the glue beads of adhesive 79 are continuous extending uninterrupted from one end edge 32 of the diaper to the other end edge 32. In addition, each juncture line 78 is shown in FIG. 4 as comprising a single bead of adhesive 79. However, the juncture line 78 may comprise more than a single bead of adhesive 79 as is shown in FIG. 4. For example, each juncture line 78 may comprise a plurality of glue beads of hot melt adhesive.

Figure 5:
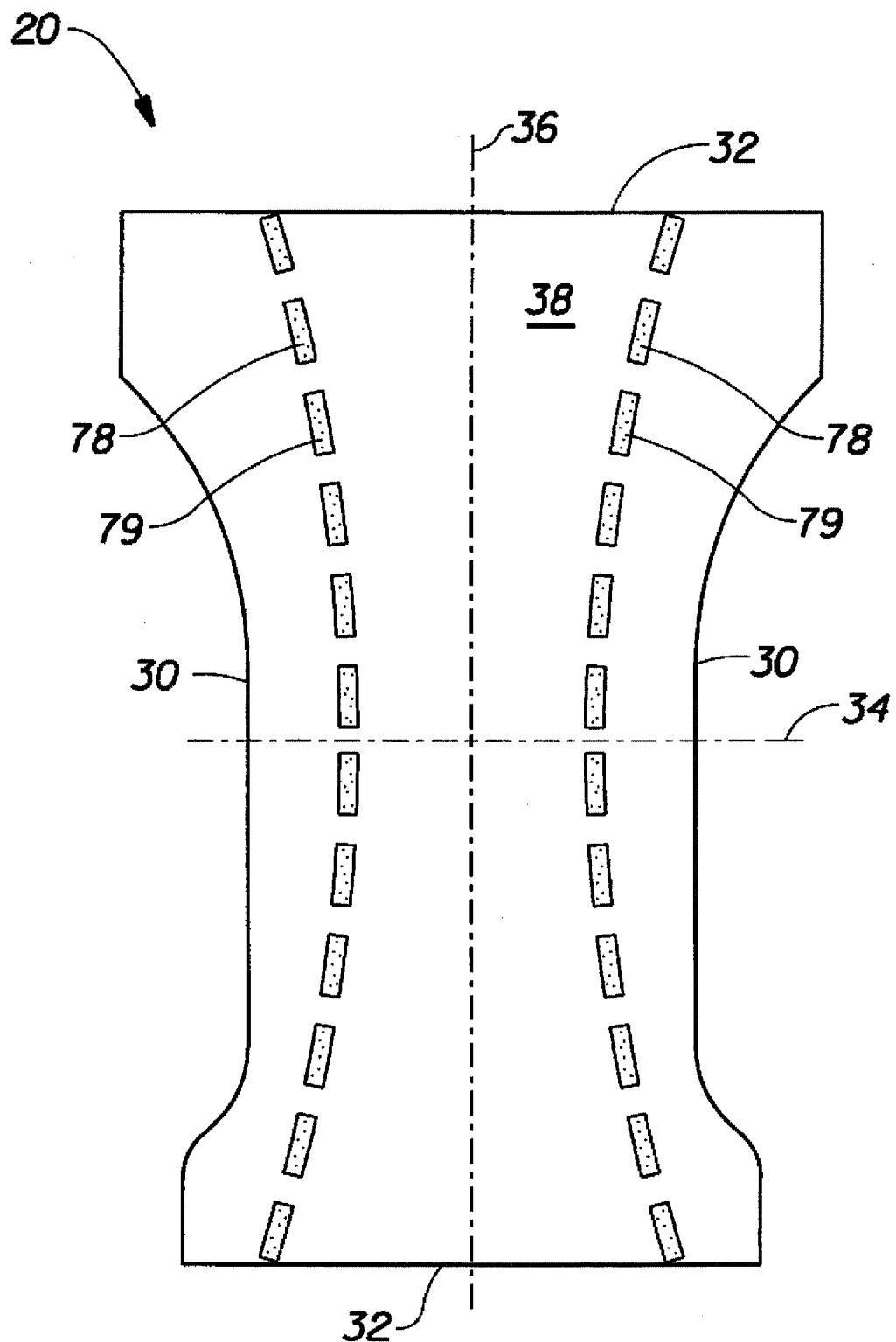
FIG. 5 is an alternative embodiment of a disposable diaper having the adhesive applied in a curved configuration.

In an alternative embodiment shown in FIG. 5, the juncture line 78 comprises an intermittent pattern of hot melt adhesive 79. The intermittent pattern of hot melt adhesive 79 extends from one end edge 32 of the diaper 20 to the opposite end edge 32 to form an intermittent curved juncture line 78.

Referring again to FIG. 3, after the adhesive has been applied in a curved configuration by adhesive applicator 104 to disposable diaper 20, a barrier leg cuff material 112 is provided. Barrier leg cuff material 112 is unwound from supply roll 110. Typically, a pair of supply rolls of leg cuff material are provided to produce a pair of barrier leg cuffs on the disposable diaper 20 as is shown in FIG. 1. The barrier leg cuff material 112 has a first edge and a second edge. As the barrier leg cuff material 112 is unwound from roll 110 at least one edge of the barrier leg cuff material, either the first edge or the second edge, is maintained parallel to the longitudinal centerline of the disposable diaper 20. Typically, both the first and second edges of the barrier cuff will be maintained parallel to the longitudinal centerline of the diaper. In other words, the edges of the barrier cuff are maintained parallel to the machine direction. An applicator 120 applies pressure to the barrier leg cuff material 112 to bond the barrier cuff to the juncture line 78. In addition, applicator 120 cuts barrier leg cuff material 112 between adjacent disposable diapers 20.

Figure 6:
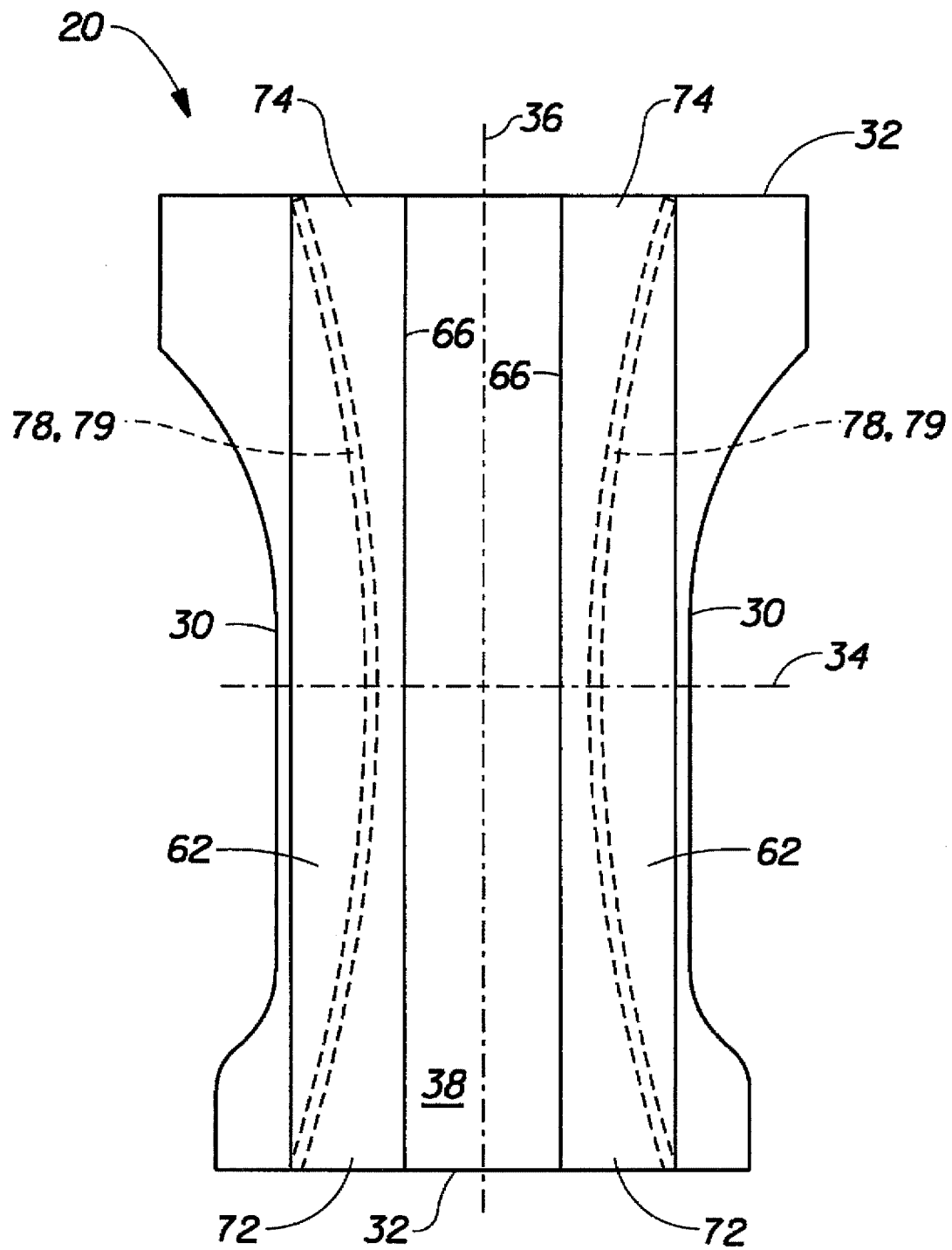
FIG. 6 is a disposable diaper of the present invention showing the diaper after the barrier cuffs have been applied and secured to the curved adhesive zones.

FIG. 6 is a plan view of the disposable diaper 20 after the barrier leg cuffs 62 have been bonded to the curved juncture line 78. When the barrier leg cuffs 62 are applied to the disposable diaper 20 at least one edge of the respective barrier leg cuffs 62 are maintained in a generally parallel relationship to the longitudinal centerline 36 of the absorbent article of the disposable diaper 20. This allows the barrier leg cuffs to be applied using conventional equipment while only requiring that the adhesive be applied to the diaper in a curved configuration. The method of the present invention avoids the use of the complex methods and equipment of the prior art which manipulate the barrier leg cuff during manufacture to form a curved barrier leg cuff.

The diaper 20 is applied to a wearer by positioning the back waist region 24 under the wearer's back, and drawing the remainder of the diaper 20 between the wearer's legs so that the front waist region 22 is positioned across the front of the wearer. The ends of the tape tab fasteners 54 are then secured to outwardly facing areas of the diaper 20. In this manner, the barrier cuff 62 should be disposed in the crotch region of the wearer. Once applied, the distal edges 66 of the barrier cuff 62 will extend through the drawing areas and will readily conform to the legs of the wearer due to the configuration of the curved adhesive zone which secures the barrier cuff 62 to the diaper 20.

In another embodiment, the disposable diaper may also comprise gasketing cuffs as described in U.S. Pat. No. 3,860,003 issued to Buell on Jan. 14, 1975, and which patent is incorporated herein by reference.

Figure 7:
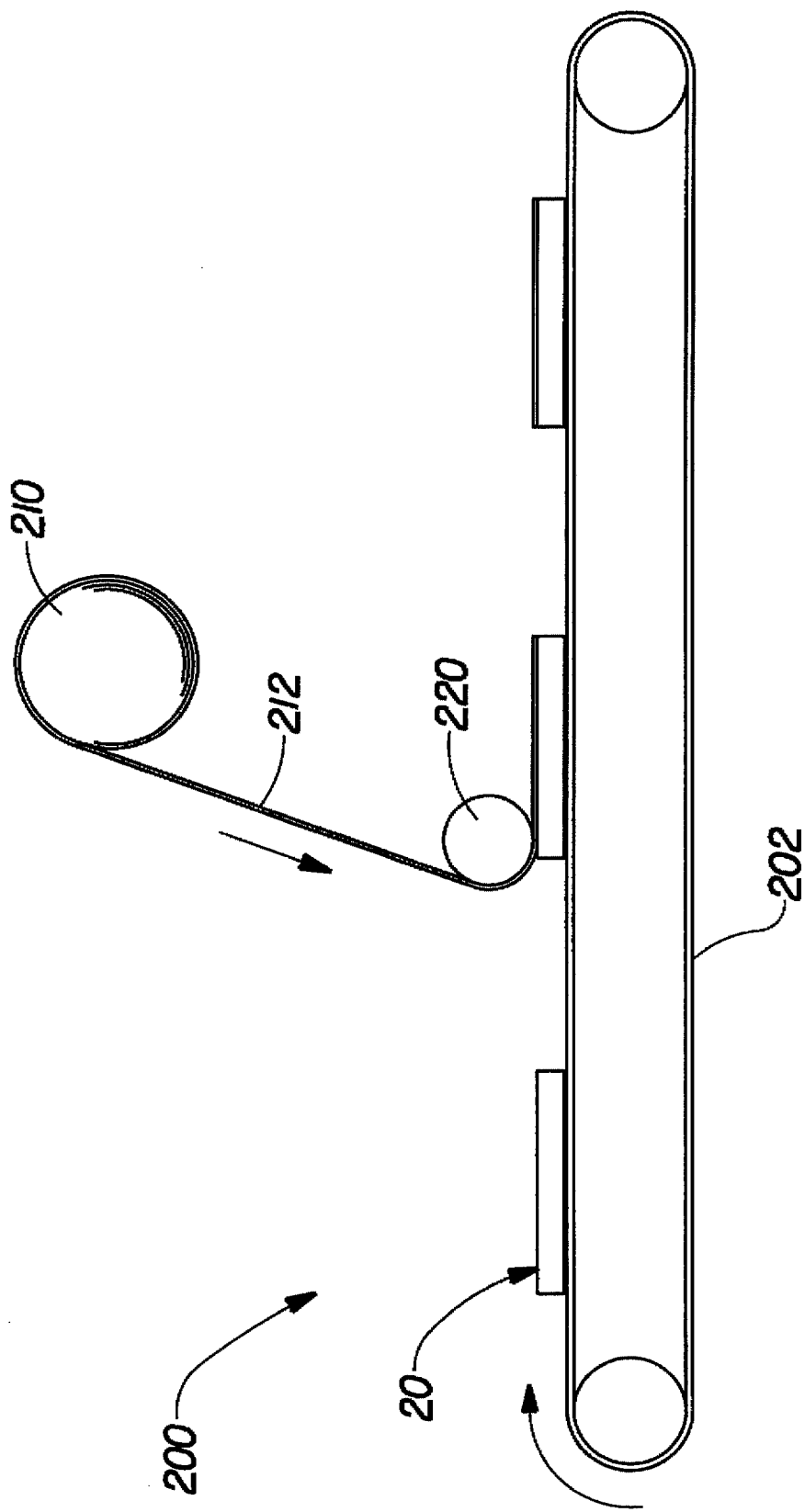
FIG. 7 is a simplified sectional side view showing another embodiment of a method for attaching the barrier cuff to the disposable diaper of the present invention.

Referring now to FIG. 7, there is shown another method and apparatus for securing a barrier leg cuff to a disposable diaper. Examining apparatus 200 in greater detail, a plurality of diapers 20 are provided and are fed on conveyor 202 towards applicator 220. A barrier leg cuff material 212 is provided and is unwound from supply roll 210. Preferably, a pair of supply rolls are provided to produce a pair of as barrier leg cuffs. The barrier leg cuff material 212 has a first edge and a second edge. As the barrier leg cuff material 212 is unwound from supply roll 210 at least one edge of the barrier leg cuff material 212, either the first edge or the second edge, is monitored parallel to the longitudinal centerline of the diaper 20. Applicator 120 bonds the barrier leg cuff materials 212 to diaper 20 along a juncture line which extends in a curved configuration with respect to the longitudinal centerline of the diaper 20. The barrier leg cuff material may be bonded to diaper 20 by ultrasonic bonding, heat bonding, pressure bonding, friction bonding, or autogenous bonding. After the barrier leg cuff material 212 has been bonded to diaper 20 along a curved juncture line, the applicator 220 cuts the barrier leg cuff material 212 between adjacent diapers 20.

The applicator is shown as comprising a single element for simplification. However, the applicator may comprise a plurality of elements which perform the functions mentioned above.

While particular embodiments of the present invention have been illustrated and described, it would be obvious to those skilled in the art that various other changes and modifications can be made without departing from the spirit and scope of the invention. It is therefore intended to cover in the appending claims all such changes and modifications that are within the scope of this invention.

What is claimed is:

1. A method for attaching a barrier cuff to an absorbent article, said method comprising the steps of:
   (a) providing an absorbent article having a longitudinal centerline and a transverse centerline perpendicular to said longitudinal centerline;
   (b) providing a barrier cuff having a first edge and a second edge;
   (c) maintaining at least one edge of said barrier cuff parallel to said longitudinal centerline of said absorbent article; and
   (d) bonding said barrier cuff to said absorbent article along a juncture line that extends in a curved configuration with respect to said longitudinal centerline of said absorbent article.

2. The method of claim 1 wherein said first edge of said barrier cuff is maintained parallel to said longitudinal centerline of said absorbent article.

3. The method of claim 1 wherein said second edge of said barrier cuff is maintained parallel to said longitudinal centerline of said absorbent article.

4. The method of claim 1 wherein said bonding step comprises a method selected from the following group: ultrasonic bonding, heat bonding, pressure bonding, adhesive bonding, friction bonding or autogenous bonding.

5. The method of claim 1 wherein said bonding is continuous.

6. The method of claim 1 wherein said bonding is intermittent.

7. The method of claim 1 wherein said barrier cuff comprises at least one spacing elastic member.

8. The method of claim 1 wherein said absorbent article comprises a disposable diaper.

9. The method of claim 1 wherein said absorbent article comprises a topsheet, a backsheet joined to said topsheet, and an absorbent core positioned between said topsheet and said backsheet.

10. The method of claim 9 wherein said barrier cuff is bonded to said topsheet.

11. A method for attaching a barrier cuff to an absorbent article comprising a topsheet, a backsheet joined to said topsheet, and an absorbent core positioned between said topsheet and said backsheet, said method comprising the steps of:
   (a) providing an absorbent article having a longitudinal centerline and a transverse centerline perpendicular to said longitudinal centerline;
   (b) providing a barrier cuff comprising at least one spacing elastic member and having a first edge and a second edge;
   (c) maintaining at least one edge of said barrier cuff parallel to said longitudinal centerline of said absorbent article; and
   (d) bonding said barrier cuff to said absorbent article along a juncture line that extends in a curved configuration with respect to said longitudinal centerline of said absorbent article.

12. The method of claim 11 wherein said bonding step comprises a method selected from the following group: ultrasonic bonding, heat bonding, pressure bonding, adhesive bonding, friction bonding or autogenous bonding.

13. The method of claim 11 wherein said bonding is continuously.

14. The method of claim 11 wherein said bonding is intermittent.

15. The method of claim 11 wherein said barrier cuff is bonded to said topsheet.

16. The method of claim 11 wherein said barrier cuff is bonded to said backsheet.

17. The method of claim 11 wherein said absorbent article comprises a disposable diaper.

\* \* \* \* \*